(12) United States Patent
Wilser et al.

(10) Patent No.: US 7,500,954 B2
(45) Date of Patent: Mar. 10, 2009

(54) EXPANDABLE ULTRASOUND TRANSDUCER ARRAY

(75) Inventors: Walter T. Wilser, Cupertino, CA (US); John Paul Mohr, Aptos, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 343 days.

(21) Appl. No.: 11/233,779

(22) Filed: Sep. 22, 2005

(65) Prior Publication Data
US 2007/0066902 A1 Mar. 22, 2007

(51) Int. Cl.
*A61B 8/12* (2006.01)
(52) U.S. Cl. .................. 600/467; 600/463; 600/459
(58) Field of Classification Search .......... 600/459, 600/467, 450; 439/77
See application file for complete search history.

(56) References Cited
U.S. PATENT DOCUMENTS 6,097,607 A * 8/2000 Carroll et al. ............. 361/752
6,129,672 A * 10/2000 Seward et al. ............. 600/463
6,238,346 B1 * 5/2001 Mason ...................... 600/459
6,605,084 B2 * 8/2003 Acker et al. ............... 606/28
2002/0049383 A1 4/2002 Swanson et al.
2005/0215895 A1 * 9/2005 Popp et al. ................. 600/437
2006/0075818 A1 * 4/2006 Huang et al. ............... 73/649
2006/0276711 A1 * 12/2006 Yuan et al. ................. 600/437
2007/0013264 A1 * 1/2007 Wilser et al. ............... 310/311
2007/0013269 A1 * 1/2007 Huang ....................... 310/334
2007/0078345 A1 * 4/2007 Mo et al. ................... 600/459
2007/0197918 A1 * 8/2007 Vitek et al. ................. 600/459
2007/0239011 A1 * 10/2007 Lau et al. ................... 600/439

OTHER PUBLICATIONS

U.S. Appl. No. 11/181,520, filed Jul. 13, 2005.

* cited by examiner

*Primary Examiner*—Eric F Winakur
*Assistant Examiner*—Helene Bor

(57) ABSTRACT

A foldable transducer array is unfolded or deployed for use, providing a larger radiating surface. While folded, the transducer array has a smaller width or volume for insertion into and withdrawal from the patient.

13 Claims, 1 Drawing Sheet

EXPANDABLE ULTRASOUND TRANSDUCER ARRAY

BACKGROUND

The present embodiments relate to ultrasound transducer arrays. In particular, ultrasound transducer arrays for improved imaging are provided. The imaging resolution, signal-to-noise ratio, depth-of-field and output power for ultrasound are a function of the size of the transducer array. Larger arrays may be able to provide improved imaging or therapy.

The space available for an ultrasound transducer array may be limited. For example, some ultrasound transducer probes are adapted for scanning from within a patient. Endocavity, transesophageal, intravascular, cardiac or other probes are sized for ease of use and patient comfort. For example, a catheter with an ultrasound transducer array is about 10 French or less in diameter. The transducer array for imaging is positioned within this small catheter.

The imaging array is used to image within the patient, such as imaging a therapeutic tool relative to tissue of interest. The distance between the imaging array of a cardiac catheter and an RF catheter for treatment of Atrial Fibrillation may be as much as 6-12 cm. Given the size of the imaging array, the RF catheter may be beyond the useful imaging focal zone.

BRIEF SUMMARY

By way of introduction, the preferred embodiments described below include methods, transducer arrays and systems for ultrasound imaging and/or therapy. A foldable transducer array is unfolded or deployed for use, providing a larger radiating and receiving surface. While folded, the transducer array has a smaller width or volume for insertion into and withdrawal from the patient.

In a first aspect, an ultrasound transducer array is provided. A first segment has at least a first element of the ultrasound transducer array. A second segment has at least a second element of the ultrasound transducer array. A bendable joint is operable to connect the first segment with the second segment in a more open position and a more closed position.

In a second aspect, a method is provided for using an ultrasound transducer array. The ultrasound transducer array is unfolded. With the array in the unfolded position, the array is used for transducing.

In a third aspect, a method is provided for acoustically transducing from a probe. The probe is inserted into a patient with an ultrasound transducer array within or on the probe. The ultrasound transducer array is expanded. The expanded ultrasound transducer array has at least two dimensions greater than a diameter of the probe during insertion.

The present invention is defined by the following claims, and nothing in this section should be taken as a limitation on those claims. Further aspects and advantages of the invention are discussed below in conjunction with the preferred embodiments and may be later claimed independently.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A folding transducer provides a smaller physical width, length or volume during insertion and unfolds once deployed to provide a larger acoustic aperture. A flexible link connects two or more element segments in parallel to form a larger array radiating face. The flexible link allows the transducer array to fold and unfold. An array with a larger aperture may have greater SNR, improved electrical impedance matching to cables, narrower acoustic beam in the focal zone, greater penetration and/or greater depth-of-field. If the transducer serves as a therapeutic tool with or without imaging capability, the wider aperture may allow greater focal gain and/or a lower F-number, providing more directed energy dissipation and/or lower power levels.

Figure 1A:
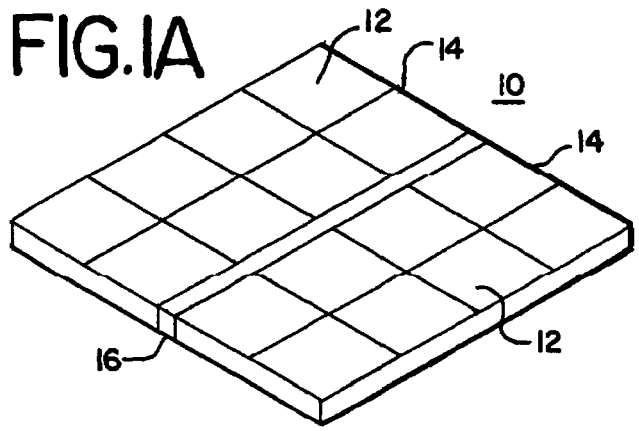
FIGS. 1A and B are perspective views of one embodiment of a foldable transducer array.

FIGS. 1A and B show an ultrasound transducer array 10. The transducer array 10 is a capacitive micromachined ultrasound transducer (CMUT), piezoelectric or other array of elements 12. The transducer array 10 is a one or multidimensional array, such as a 1.25D, 1.5D, 1.75D or two-dimensional array of elements 12.

As a cMUT array, one or more flexible membranes are provided over respective chambers or gaps for each element 12. An electrode positioned on the membrane and another electrode positioned within the chamber or gap in conjunction with the flexibility of the membrane transduce between electrical and acoustical energies. The transducer element 12 is formed using either CMUT or other micro-electro mechanical manufacturing techniques, such as semiconductor manufacturing techniques. Other substrate based, micro-electro mechanical, or capacitive based transducer elements may be used. For example, a beam rather than a membrane is provided. A hole, gap or other structures may be provided through the membrane, such as a hole used for etching away insulator material to form the chamber. As a piezoelectric array, piezoelectric material is separated into separate elements 12.

The transducer 10 includes a plurality of segments 14 and one or more joints 16. Additional, different or fewer components may be provided. For example, additional segments 14 and corresponding joints 16 are provided, such as for use in a 64, 96, 128 or other number of element one-dimensional array.

Each segment 14 includes one or more elements 12 of transducer material, such as a PZT slab, PZT composite or semiconductor substrate of a cMUT. For cMUT elements 12, the segments 14 are slabs of semiconductor or other material that can be processed to form the transducer elements and electrical interconnections. For example, the segments 14 are formed from a silicon wafer. Other semiconductor materials may be used. Slab is used as a general term for a plate, strip, block, beam, or other shape. The segments 14 are formed from a same wafer, so have similar structures. Alternatively, different wafers are used for different segments 14. For PZT or composite elements 12, the segments 14 are slabs of PZT or composite material. The transducer material is diced and filled to form individual elements 12. The same or different transducer material is used for each segment 14. A backing block, matching layers, ground plane and/or signal electrodes (e.g., flexible circuit) are also provided for each segment 14.

The segments 14 are positioned adjacent to each other, such as each segment 14 being within at least one element width of another one of the segments 14. The segments 14 are in contact with additional segments 14, closely abutted or provide minimized space for rotation given the thickness and amount of rotation.

The segments 14 are a same or different size. For example, each segment 14 includes a same or different number of elements 12. FIG. 1A shows two rows and four columns of elements 12 for each segment 14, but the segments 14 may be asymmetric. Each segment 14 provides a multidimensional array of elements 12, but a one-dimensional or a single element array may be provided on each segment 14. For example, each segment 14 provides a 32×1 or 64×1 group of elements 12. A fewer or greater number of columns and/or rows may be used.

Each segment 14 includes conductors on a same or opposite side of the segments 14. For example, a via routes signal traces or ground connections to different surfaces of the segment 14. The different conductors are signal traces, vias, doped-silicone, or other conductors connected with each element 12 separately or in common. One conductor provides signal electrodes of the elements 12. Another conductor provides bias voltages to the elements 12. Yet another conductor provides grounding connections to the elements 14. For use as a completely independently activated array of elements 12, a different signal conductor is provided for each element 12. For use in a walking aperture, the same signal conductor may connect with all or some of the elements 12 in a row of elements 12. The same biased voltage conductor connects with all the elements 12 or a subset elements 12. For example for use in a walking aperture, different bias voltage conductors are provided for different columns of elements 12. Bias voltage conductors can be used for selectively activating the different rows. Other arrangements of electrical connection to, between, within and/or through the elements 12 may be provided.

In another embodiment, one or more of the segments 14 include electronics, such as amplifiers, multiplexers or switches. The electronics are provided on the same substrates as the elements 12. Alternatively, one or more of the segments 14, such as segments 14 on the ends of the array 10 or spaced within the array 10, include the electronics without any elements 12. The segments 14 with the electronics electrically connect with one or more other segments 14 across the joint 16. The electronics are then provided as part of the array 10, such as in a catheter.

The joint 16 is bendable, such as flexible conductive material or other flexible material or a hinge. The bendable joint 16 connects one segment 14 with another segment 14. The connection is along an entire or a portion of an edge of each segment 14. One joint 16 may connect three or more segments 14. Multiple joints 16 may connect two or more segments 14 together. The joint 16 is thin, such as being less than half an element width, but wider joints 16 may be used.

Figure 1B:
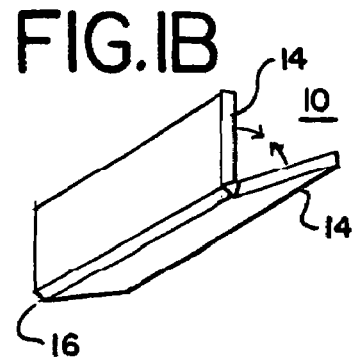

The joint 16 allows one segment 14 to rotate relative to another segment 14 about the joint 16. FIG. 1B shows two segments 14 rotating closer together into a folded position. A folded position is a relative term indicating the ultrasound transducer array 10 in a more closed position than when unfolded. For example, folded corresponds to a more closed 170 degrees between the segments 14 about the hinge 16 than an open position of 180 degrees. As another example, folded corresponds to less than 20, 45, 90 or other number of degrees and unfolded corresponds to greater than 90, 120, 135, 170 or other number of degrees. The more open position is a deployed position for transducing, and the more closed position is an undeployed position for minimizing space.

Figure 2:
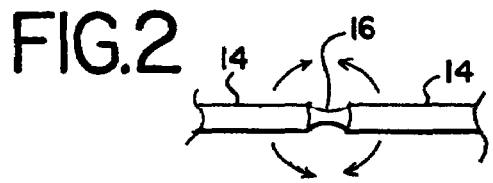
FIG. 2 is a partial view of a first embodiment of a joint of the array of FIGS. 1A and B.

FIG. 2 shows one embodiment of the joint 16. The joint 16 is flexible or bendable material, such as polymer, rubber based material or memory metal. The joint 16 narrows between the segments 14 for greater freedom of bending or folding, but may be even with or bulge relative to the faces of the segments 14. In one embodiment, electrical connections are through vias or around edges of each segment 14 and do not extend over or through the joint 16 between different segments 14. For example, electrical traces extend over an edge of each segment connected by the joint 16. Alternatively, one or more electrodes (e.g., grounding plane) or conductive traces are deposited or formed on or in the joint 16 for electrically interconnecting the adjoining segments 14.

Figure 3:
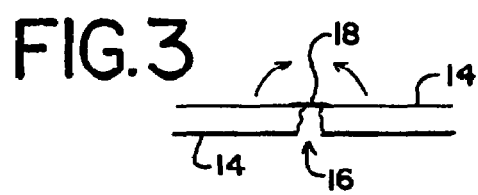
FIG. 3 is a partial view of a second embodiment of a joint of the array of FIGS. 1A and B.

FIG. 3 shows another embodiment of the joint 16. The joint 16 is a flexible conductor or metal, such as gold, copper, silver, other metal or other now known or later developed conductor that is flexible enough to withstand folding and unfolding. The joint 16 is a few microns thick, but greater or less thicknesses may be provided depending on the degree of flexibility. The joint 16 is formed while the segments 14 are connected together or are a common substrate. Using lithography, metallization, patterning, etching, depositing, sputtering or other semiconductor process, the joint 16 extending between sections of a common substrate that will become two different segments 12 is formed. The conductor of the joint 16 is used electrically for interconnecting the segments 14 or may be used without electrical connection.

Figure 4:
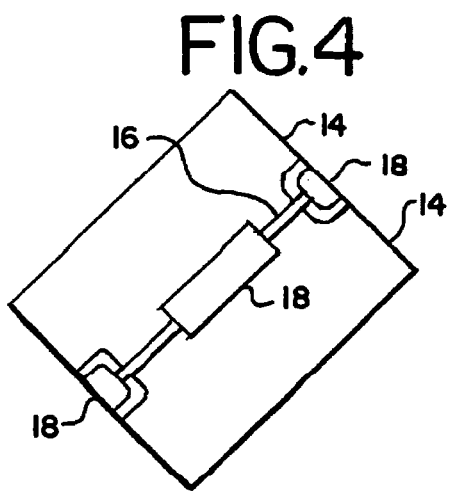
FIG. 4 is a top perspective view of the foldable transducer array with the joint of FIG. 3.

In one embodiment, the joint 16 is a flat bridge structure with an air gap underneath. For example, gold is deposited over an insulator by sputtering. The sputtered gold is patterned, such as forming an isolation gap between different ones of electrical connectors 18. FIG. 4 shows the joint 16 with three different or isolated electrical connectors 18. The electrical connectors 18 are routed from a same or different sides or faces of the segments 14, such as routing signal electrodes from a bottom to a top of each segment. The electrical connectors 18 are isolated from each other to connect different electrodes, such as a ground plane being routed separately from different signal or bias traces. The electrical connectors 18 extend between the different segments 14 in a generally same plane. The insulator is etched or diced away leaving an air gap and forming a conductive sheet. For example, the end pads or small electrical connector 18 connect electrodes wrapped around from the backside of the segments 14 together, and the middle pad or larger electrical connector 18 connects electrodes the front side of the segments 14 together. In an alternative embodiment, the joint 16 is formed as a bridge or arching structure on the common substrate. Electroplating or evaporation can also be used to deposit the electrical connectors 18.

Figure 5:
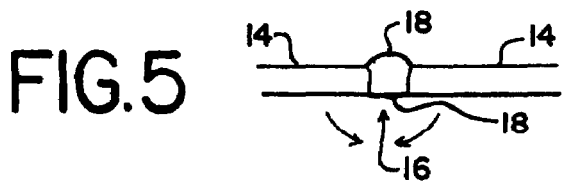
FIG. 5 is a partial view of a third embodiment of a joint of the array of FIGS. 1A and B.

FIG. 5 shows another embodiment of the joint 16. The joint 16 includes two layers of electrical connectors 18, one on the top surface and another on the bottom surface 16. One or both of the two electrical connectors 18 are arched as a bridge structure, such as being arched away from the opposing electrical connector 18. Arching towards an opposing electrical connector 18 may be provided. The joint 16 is formed by depositing the electrical connectors 18, such as depositing or patterning gold, over a sacrificial insulation layer. The insulation layer is shaped to provide the desired electrical connector shape, such as flat on one surface and arched or longer on another surface. The insulator is etched away, providing the flexible joint 16.

Figure 6:
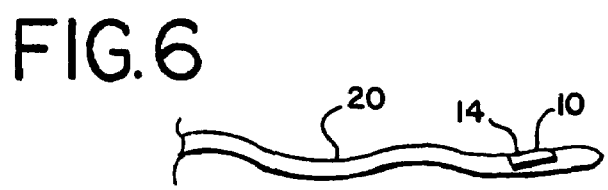
FIGS. 6 and 7 are illustrations of a foldable transducer array on a catheter.
Figure 7:

FIGS. 6 and 7 show incorporation of the array 10 into or on a catheter 20 (e.g., intravascular or cardiac catheter), transesophageal probe, endocavity probe, vaginal probe, endorectal probe, or other probe operable within a patient's body. The array 10 is positioned within an outer sheath of the catheter 20. The outer sheath is flexible and/or expandable, such as being formed of a balloon, polymer or rubber material. Alternatively, the array 10 is connected to the catheter 20 outside of the catheter housing. Alternatively, the array 10 is positioned within or on a probe for use externally of a patient, such as a handheld probe.

The array 10 is deployable. FIG. 6 shows the array in a folded position, and FIG. 7 shows the array in a deployed or unfolded position. A mechanism folds and unfolds the array. For example, wires with gears, belts, pulleys or other structure connect with the segments 14 to open and close the array 10. The joint 16 or one of the segments 14 remains generally in one location, such as being affixed to the catheter. Mechanical force is then applied to open or close the array 10. As another example, a motor with gears or wires within the probe opens and closes the array 10. As yet another example, the segments 14 are connected with or fixed to a balloon or other expandable and contractible structure. By adding or removing gas, such as air, or fluid, the balloon expands and contracts, folding and unfolding the array. The catheter sheath may also be a balloon that expands with the array by pumping in an acoustically matching fluid. As another example, a thermally or electrically activated memory material, such as a memory metal, connects with one or more segments 14 to move the segments 14 in response to thermal or electrical energy. The joint 16 may comprise memory material operable to fold and unfold the segments 14. Multiple mechanisms may be used to fold the array for withdrawal from the patient or unfold the array for use.

Figure 8:
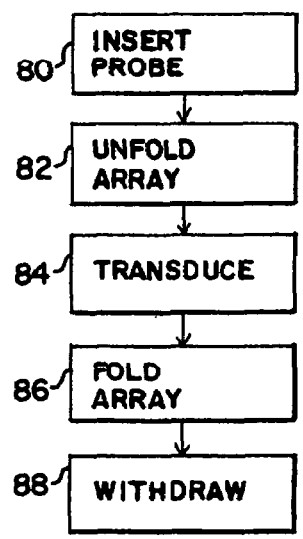
FIG. 8 is a flow chart diagram of one embodiment of a method for using a foldable ultrasound transducer array.

FIG. 8 shows one embodiment of a method for using an ultrasound transducer array, such as a method for acoustically transducing from a probe. The method uses the ultrasound transducer arrays 10 described above in FIGS. 1A-7 or other transducer arrays. Additional, different or fewer acts than shown in FIG. 8 may be provided. For example, the method may be provided without the inserting, transducing or withdraw of acts 80, 84 or 88. The acts may be performed in a different order than shown in FIG. 8.

In act 80, the probe is inserted into a patient. For a catheter, the probe may be inserted through a vessel. Alternatively, the probe is inserted into a body cavity. The probe includes an ultrasound transducer array for imaging. To increase patient comfort, the array is in a folded position, reducing the volume of space occupied by the probe. For example, the probe is in the catheter 20 shown in FIG. 6 with the array having a width and height less than a diameter of the catheter 20.

In act 82, the ultrasound transducer array is unfolded. For example, the array 10 of the catheter 20 shown in FIG. 7 is opened within the patient. The joint 16 between two segments 14 is flexed, bent or rotated. The angle between the segments is changed, such as opening from an angle of less than 90 degrees to an angle greater than 120 degrees (e.g., opening to 180 degrees or flat). A sensor may be provided to determine an amount of unfolding. For example, one or more elements on the array are used to determine a distance to another element on a different segment. By opening the segments, each with a plurality of transducer elements, the ultrasound transducer array has a larger acoustic face. The ultrasound transducer array is expanded so that at least two dimensions (e.g., a width or elevation dimension and a length or azimuth dimension) are each greater than a diameter of the probe during insertion in act 80. Only one dimension may be greater than the catheter diameter. A longer one-dimensional array or a wider a multidimensional transducer array are formed by unfurling the array. Alternatively, the array is unfolded but still has all three dimensions less than the diameter of the catheter.

In act 84, the opened array is used to transduce between acoustic and electrical energy. In the expanded or unfolded position, the array provides a wider aperture for imaging or therapy. Electrical signals are provided to the different elements of the array. With relative delays and apodization, the acoustic energy generated in response to the electrical signals is focused along on or more scan lines, in a plane or as a diverging wavefront. As a multidimensional array, electric steering is provided to scan a volume or focus in elevation. For imaging, the elements of the transducer array transducer acoustic echoes into electrical signals. Using relative delays and apodization, the received electrical signals are beamformed or otherwise processed into samples representing the scanned region. Images indicating tissue or tools of interest are formed. Since a larger aperture is provided, more information or information provided by the larger aperture may aid diagnosis or therapy. For example, three-dimensional imaging with a multidimensional array may improve the workflow for ablation therapy or valve repair or replacement.

In act 86, the array is folded or refurled. The array is folded to reduce the width or space occupied by the array. One, two or more mechanisms for folding the array are operated. Once in a stowed position, the probe is withdrawn in act 88.

The probe is a single use device in one embodiment. The entire probe or a portion of the probe is not used again. Alternatively, the array, entire probe or other portions of the probe are cleaned and/or refurbished for a subsequent use. For a probe used externally to the body, the probe may be reused without cleaning or refurbishment.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. An ultrasound transducer array comprising:
   a first segment having at least a first element of the ultrasound transducer array;
   a second segment having at least a second element of the ultrasound transducer array; and
   a foldable joint operable to connect the first segment with the second segment in a deployed position and an undeployed position;
   wherein the foldable joint comprises flexible conductive material.

2. The array of claim 1 wherein the first and second segments comprise substrates of a capacitive membrane transducer.

3. The array of claim 1 wherein the first segment comprises multiple elements including the first element and the second segment comprises multiple elements including the second element, the first and second segments comprising a multidimensional transducer array.

4. The array of claim 1 further comprising the ultrasound transducer array positioned in or on a probe operable within a patient's body.

5. The array of claim 4 wherein the probe comprises an intravascular or cardiac catheter.

6. The array of claim 1 where the undeployed position comprises an angle between the first and second segments of less than 90 degrees and wherein the deployed position comprises an angle of greater than 120 degrees.

7. A method for using an ultrasound transducer array, the method comprising:
- inserting the ultrasound transducer array in a undeployed position within a catheter into a patient;
- unfolding the ultrasound transducer array at foldable joint; and
- transducing with the array in the deployed position;
- wherein transducing comprises selectively activating different rows of elements of the array in a walking aperture by transmitting electrical signals through conductors in the foldable joint.

8. The method of claim 7 wherein deploying comprises flexing a joint between two segments.

9. The method of claim 7 wherein deploying comprises changing from a first angle between said first and second segments being less than 90 degrees to a second angle of greater than 120 degrees.

10. The method of claim 7 wherein deploying the ultrasound transducer array comprises opening at least two segments each having a plurality of transducer elements, the ultrasound transducer array having a larger acoustic face when deployed than undeployed, and wherein the array during transducing comprises a multi-dimensional array of elements.

11. An ultrasound transducer array comprising:
- a first segment having at least a first element of the ultrasound transducer array;
- a second segment having at least a second element of the ultrasound transducer array; and
- a foldable joint operable to electrically connect the first segment with the second segment in a deployed position and an undeployed position;
- wherein the first and second segments are from a common substrate.

12. An ultrasound transducer array comprising:
- a first segment having at least a first element of the ultrasound transducer array;
- a second segment having at least a second element of the ultrasound transducer array; and
- a foldable joint operable to connect the first segment with the second segment in a more open position and a more closed position, the foldable joint including multiple layers of electrical conductors.

13. The ultrasound transducer of claim 12 wherein the multiple layers comprise a first layer connected with top surfaces of the first and second segments and a second layer connected with bottom surfaces of the first and second segments.

* * * * *